(12) United States Patent
Barr

(10) Patent No.: US 8,864,813 B2
(45) Date of Patent: Oct. 21, 2014

(54) BALLOON/SELF-EXPANDING STENT GRAFT

(75) Inventor: Aaron P. Barr, Fishers, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 1513 days.

(21) Appl. No.: 11/630,921

(22) PCT Filed: Jun. 30, 2005

(86) PCT No.: PCT/US2005/023491
§ 371 (c)(1),
(2), (4) Date: Aug. 16, 2007

(87) PCT Pub. No.: WO2006/014347
PCT Pub. Date: Feb. 9, 2006

(65) Prior Publication Data
US 2008/0039927 A1   Feb. 14, 2008

Related U.S. Application Data

(60) Provisional application No. 60/585,314, filed on Jul. 2, 2004.

(51) Int. Cl.
*A61F 2/06* (2013.01)
*A61F 2/07* (2013.01)
*A61F 2/89* (2013.01)
*A61F 2/848* (2013.01)
*A61F 2/95* (2013.01)

(52) U.S. Cl.
CPC ... *A61F 2/07* (2013.01); *A61F 2/89* (2013.01); *A61F 2220/0016* (2013.01); *A61F 2230/0054* (2013.01); *A61F 2/848* (2013.01); *A61F 2002/9517* (2013.01); *A61F 2220/0075* (2013.01); *A61F 2220/0008* (2013.01); *A61F 2/95* (2013.01); *A61F 2002/075* (2013.01); *A61F 2230/0067* (2013.01); *A61F 2002/9511* (2013.01); *A61F 2250/0063* (2013.01); *A61F 2230/005* (2013.01)
USPC .......................................................... 623/1.13

(58) Field of Classification Search
USPC ................... 623/1.13, 1.16, 1.18, 1.2, 1.36
See application file for complete search history.

(56) References Cited

U.S. PATENT DOCUMENTS

| | | | | |
|---|---|---|---|---|
| 4,801,299 A * | 1/1989 | Brendel et al. | ............... | 623/1.47 |
| 5,695,517 A | 12/1997 | Marin et al. | ............... | 606/198 |
| 6,168,621 B1 * | 1/2001 | Vrba | ............... | 623/1.2 |
| 6,290,731 B1 * | 9/2001 | Solovay et al. | ............... | 623/1.16 |
| 6,336,937 B1 * | 1/2002 | Vonesh et al. | ............... | 623/1.13 |
| 6,945,994 B2 * | 9/2005 | Austin et al. | ............... | 623/1.16 |
| 7,037,327 B2 * | 5/2006 | Salmon et al. | ............... | 623/1.11 |
| 7,147,661 B2 * | 12/2006 | Chobotov et al. | ............... | 623/1.16 |
| 2002/0198587 A1 * | 12/2002 | Greenberg et al. | ............... | 623/1.13 |
| 2003/0014126 A1 * | 1/2003 | Patel et al. | ............... | 623/23.72 |
| 2003/0199967 A1 * | 10/2003 | Hartley et al. | ............... | 623/1.13 |

* cited by examiner

*Primary Examiner* — Thomas McEvoy
*Assistant Examiner* — Julie A Szpira
(74) *Attorney, Agent, or Firm* — Brinks Gilson & Lione

(57) ABSTRACT

An intraluminal prosthesis for strengthening a lumen. The prosthesis may include a tubular graft (50) comprising a hollow flexible body (20). A self-expanding stent (19) may be coupled to the body (20) that provides enough outward radial force to expand the body. The prosthesis also includes a tubular stent (17). The tubular stent has a first diameter and a second expanded diameter. The tubular stent (17) is formable to the second diameter by application of an outwardly extending force from the interior of the tubular stent. The second diameter is at least equal to the interior diameter of the hollow flexible body (20).

20 Claims, 14 Drawing Sheets

BALLOON/SELF-EXPANDING STENT GRAFT

BACKGROUND OF THE INVENTION

1. Technical Field

This invention relates to a medical device and, in particular, a prosthesis for implantation within the human or animal body for the repair of an aneurism, dissection, or intramural hematoma within a lumen, and a method for implanting the same.

2. Related Art

Throughout this specification, when discussing the aorta or other blood vessels, the terms distal and distally with respect to a prosthesis are intended to refer to the end of the prosthesis furthest away in the direction of blood flow from the heart. Similarly, the terms proximal and proximally are intended to mean the end of the prosthesis which, when implanted, would be nearest to the heart.

The functional vessels of humans, such as blood vessels and ducts, occasionally weaken or even rupture. For example, the aortic wall can weaken, resulting in an aneurysm Upon further exposure to haemodynamic forces, such an aneurysm can rupture. A common surgical intervention for weakened, aneurismal or ruptured vessels is the use of a prosthesis to provide some or all of the functionality of the original, healthy vessel and/or preserve any remaining vascular integrity by replacing a length of the existing vessel wall that spans the site of vessel failure.

The deployment of intraluminal prostheses into the lumen of a patient from a remote location by the use of a deployment device or introducer has been disclosed in a number of earlier patents, published patent applications, and other publications. U.S. Pat. No. 4,562,596, entitled "Aortic Graft, Device and Method for Performing an Intraluminal Abdominal Aortic Aneurysm Repair" which is herein incorporated by reference, proposes the retention of a self expanding graft within a sleeve until it is to be deployed, at which time the sleeve is withdrawn and the graft is allowed to expand. U.S. Pat. No. 4,665,918, entitled "Prosthesis System and Method" which is herein incorporated by reference, proposes a system and method for the deployment of a prosthesis in a blood vessel. The prosthesis is positioned between a delivery catheter and an outer sheath and expands outwardly upon removal of the sheath.

U.S. Pat. No. 4,950,227, entitled "Stent Delivery System" which is herein incorporated by reference, proposes the delivery of a stent by mounting the stent to the outside of an inflatable catheter and retaining the ends of an unexpanded stent by fitting a sleeve over either end of the stent. Expansion of the stent is caused by inflation of the catheter between the sleeves so that the ends of the stent are withdrawn from the respective sleeves and the stent released and expanded into position.

Other clinical approaches to aneurysm repair known as endovascular grafting have been proposed. (See, Parodi, J. C., et al. "Transfemoral Intraluminal Graft Implantation for Abdominal Aortic Aneurysms," 5 Annals of Vascular Surgery, 491 (1991)). Endovascular grafting involves the transluminal placement of a prosthetic arterial graft in the endoluminal position within the lumen of the artery. By this method, the graft is attached to the internal surface of an arterial wall by means of attachment devices such as expandable stents, a cephalic stent above the aneurysm and a caudal stent below the aneurysm.

U.S. Pat. No. 5,387,235 entitled "Expandable Transluminal Graft Prosthesis for Repair of Aneurysm", discloses apparatus and methods of retaining grafts onto deployment devices. These features and other features disclosed in U.S. Pat. No. 5,387,235 could be used with the present invention and the disclosure of U.S. Pat. No. 5,387,235 is herein incorporated by reference.

U.S. Pat. No. 5,720,776 entitled "Barb And Expandable Transluminal Graft Prostheses for Repair of Aneurysm" discloses improved barbs with various forms of mechanical attachment to a stent. These features and other features disclosed in U.S. Pat. No. 5,720,776 could be used with the present invention and the disclosure of U.S. Pat. No. 5,720,776 is herein incorporated by reference.

U.S. Pat. No. 6,206,931 entitled "Graft Prosthesis Materials" discloses graft prosthesis materials and a method for implanting, transplanting replacing and repairing a part of a patient and particularly the manufacture and use of a purified, collagen based matrix structure removed from a submucosa tissue source. These features and other features disclosed in U.S. Pat. No. 6,206,931 could be used with the present invention and the disclosure of U.S. Pat. No. 6,206,931 is herein incorporated by reference.

PCT Patent Publication Number No. WO99/29262 entitled "Endoluminal Aortic Stents" discloses a fenestrated prosthesis for placement where there are intersecting arteries. This feature and other features disclosed in PCT Patent Publication Number No. WO99/29262 could be used with the present invention and the disclosure of PCT Patent Publication Number No. WO99/29262 is herein incorporated by reference.

PCT Patent Publication Number No. WO03/034948 entitled "Prostheses for Curved Lumens" discloses prostheses with arrangements for bending the prosthesis for placement into curved lumens. This feature and other features disclosed in PCT Patent Publication Number No. WO03/034948 could be used with the present invention and the disclosure of PCT Patent Publication Number No. WO03/034948 is herein incorporated by reference.

United States Patent Application Publication No. 20030233140 entitled "Trigger Wire System" discloses release wire systems for the release of stent grafts retained on introducer devices. This feature and other features disclosed in United States Patent Application Publication No. 20030233140 could be used with the present invention and the disclosure of United States Patent Application Publication No. 20030233140 is herein incorporated by reference.

United States Patent Application Publication No. 20040098079 entitled "Thoracic Aortic Stent Graft Deployment Device" discloses introducer devices adapted for deployment of stent grafts particularly in the thoracic arch. This feature and other features disclosed in United States Patent Publication No. 20040098079 could be used with the present invention and the disclosure of United States Patent Publication No. 20040098079 is herein incorporated by reference.

United States Patent Application Publication No. 20040054396 entitled "Stent-Graft Fastening" discloses arrangements for fastening stents onto grafts particularly for exposed stents. This feature and other features disclosed in United States Patent Application Publication No. 20040054396 could be used with the present invention and the disclosure of United States Patent Application Publication No. 20040054396 is herein incorporated by reference.

PCT Patent Publication Number No. WO03/053287 entitled "Stent Graft With Improved Graft Adhesion" discloses arrangements on stent grafts for enhancing the adhesion of such stent grafts into walls of vessels in which they are deployed. This feature and other features disclosed in PCT Patent Publication Number No. WO03/053287 could be used with the present invention and the disclosure of PCT Patent Publication Number No. WO03/053287 is herein incorporated by reference.

PCT Patent Publication Number No. WO98/53761 entitled "A Prosthesis and a Method of Deploying a Prosthesis", which is herein incorporated by reference, discloses various embodiments of an introducer for positioning an expandable endovascular prosthesis in a lumen of a patient.

One issue that arises with the use of an intraluminal prosthesis is where the damage in a vessel is at or near an angled or curved portion of the lumen, such as, for example, the aortic arch. In these instances, the intraluminal prosthesis may have an increased tendency to leak. It would be desirable to provide an intraluminal prosthesis with a sealing means that provides an effective seal in an angled or curved portion of a lumen.

SUMMARY

An intraluminal prosthesis for strengthening a lumen is provided having particular utility in angulated anatomy. The prosthesis includes a tubular graft comprising a hollow body sufficiently flexible to conform to a targeted angulated anatomy. A self-expanding stent can be coupled to the body that provides enough outward radial force to expand at least a portion of the hollow flexible body. The self-expanding stent can include gripping means for gripping the walls of the lumen to hold at least a portion of the prosthesis at or adjacent to the targeted anatomy. The prosthesis can also include a tubular stent. The tubular stent can have a first diameter and a second expanded diameter. The tubular stent can be self expanding between the first and second diameter, or formable to the second diameter by application of an outwardly extending force from the interior of the tubular stent. The second diameter is desirably at least equal to the interior diameter of the targeted anatomy in which the intraluminal prosthesis is to be employed. Other features and advantages of an intraluminal prosthesis of the present invention will become apparent from the following detailed description.

The term "prosthesis" means any replacement for a body part or function of that body part. It can also mean a device that enhances or adds functionality to a physiological system. The terms "intraluminal" and "endoluminal" describes objects that are found or can be placed inside a lumen in the human or animal body. A lumen can be an existing lumen or a lumen created by surgical intervention. This includes lumens such as blood vessels, parts of the gastrointestinal tract, ducts such as bile ducts, parts of the respiratory system, etc. "endoluminal prosthesis" or "intraluminal prosthesis" thus describes a prosthesis that can be placed inside one of these lumens.

The invention can be better understood with reference to the following drawings and description. The components in the Figures are not necessarily to scale, emphasis instead being placed upon illustrating the principles of the invention. Moreover, in the Figures, like referenced numerals designate corresponding parts throughout the different views.

DETAILED DESCRIPTION OF THE PREFERRED EMBODIMENTS

Figure 1:
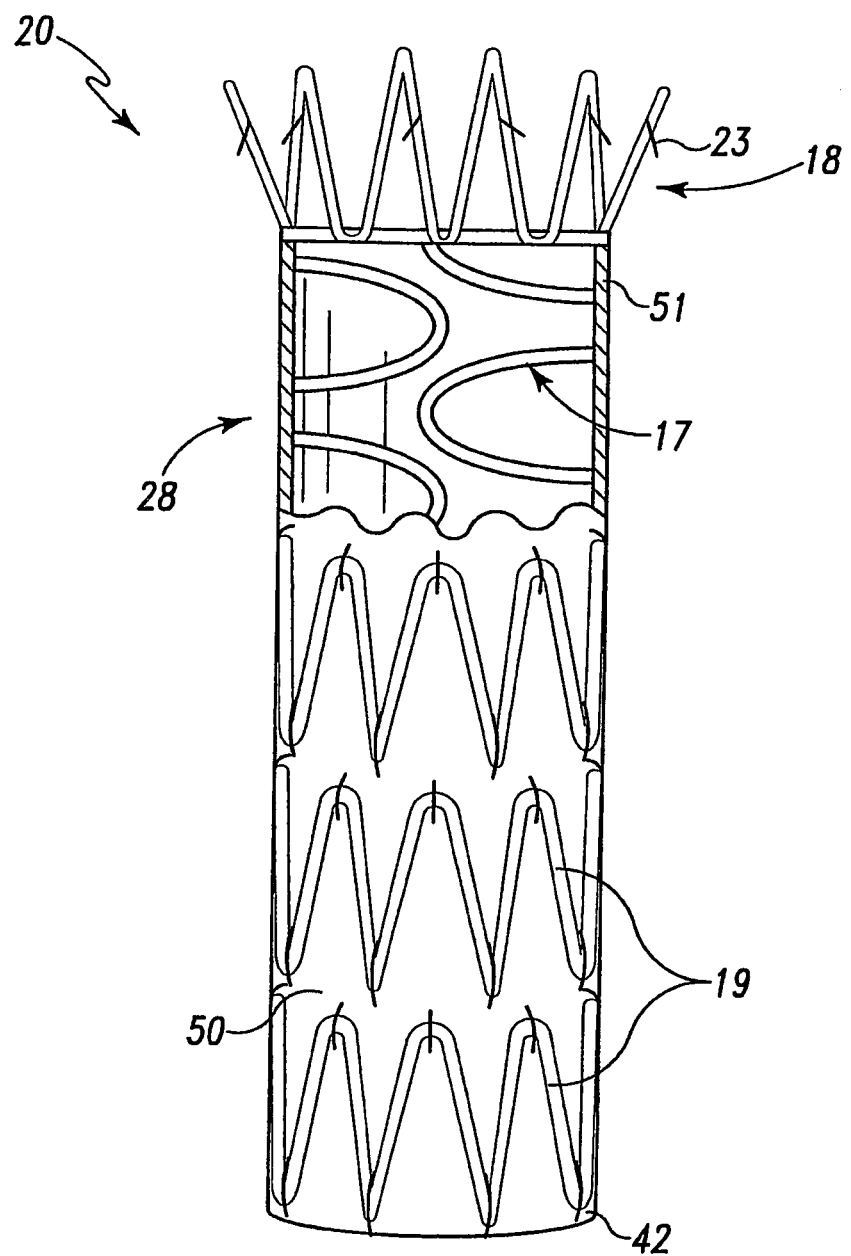
FIG. 1 is a side elevation view, partially cut away, of a prosthesis of the present invention.

A cutaway view of a prosthesis 20 of the present invention is shown in FIG. 1. The self-expanding prosthesis 20 has a tubular graft 50 that can have resilient stents 19 attached thereto to enable the prosthesis 20 to expand following its release from an introducer. The term "graft" means a generally cannular or tubular member which acts as an artificial vessel. A graft by itself or with the addition of other elements can be an endoluminal prosthesis. The term "stent" means any device or structure that adds rigidity, expansion force or support to a prosthesis.

The material forming the tubular graft 50 is preferably non-porous so that the tubular graft 50 does not leak or sweat under physiologic forces. The graft material can be made of woven DACRON® polyester (VASCUTEK® Ltd., Renfrewshire, Scotland, UK). The tubular graft 50 can also be made of any other at least substantially biocompatible material including such materials as other polyester fabrics, polytetrafluoroethylene (PTFE), expanded PTFE, and other synthetic materials known to those of skill in the art. Naturally occurring biomaterials, such as collagen, are also highly desirable for forming the tubular graft 50, particularly a derived collagen material known as extracellular matrix (ECM), such as small intestinal submucosa (SIS).

Other examples of ECMs suitable for forming tubular graft 50 are pericardium, stomach submucosa, liver basement membrane, urinary bladder submucosa, tissue mucosa, and dura mater. SIS is particularly useful, and can be made in the fashion described in U.S. Pat. No. 4,902,508 to Badylak et al.; U.S. Pat. No. 5,733,337 to Carr; 17 Nature Biotechnology 1083 (November 1999); and WIPO Publication WO 98/22158 of May 28, 1998, to Cook et al., which is the published application of PCT/US97/14855. All of these patents and publications are incorporated herein by reference.

Irrespective of the origin of the material for the tubular graft 50 (synthetic versus naturally occurring), the graft material can be made thicker by making multi-laminate constructs, for example SIS constructs as described in U.S. Pat. No. 5,968,096, U.S. Pat. No. 5,955,110, U.S. Pat. No. 5,885,619, and U.S. Pat. No. 5,711,969. All of these patents are incorporated herein by reference. In addition to xenogenic biomaterials, such as SIS, autologous tissue can be harvested as well, for use in forming the graft material. Additionally elastin or elastin-like polypeptides (ELPs) and the like offer potential as a material to fabricate the tubular graft 50.

The prosthesis 20 can include self expanding stents 19 that cause the prosthesis 20 to expand following its disengagement from a suitable introducer. The prosthesis 20 can also include a self expanding zigzag stent 18 that extends from a proximal end 51 of the tubular graft 50. The self expanding zigzag stent 18 can have gripping means in the form of hooks or barbs 23 to anchor at least the proximal end 51 of the tubular graft 50 to a selected location within a lumen in a patients body. As shown in the cutaway portion of FIG. 1, the self-expanding prosthesis 20 also includes a central portion 28, between the proximal end 51 and the self expanding stents 19, that contains a wire stent 17 having a plurality of curved sections. The wire stent 17 can be a Gianturco-Rueben type balloon-expandable stent of the type disclosed, for example, in U.S. Pat. No. 4,800,882. The self expanding stents 19 cause the prosthesis 20 to expand following its disengagement from the introducer. When the self expanding zigzag stent 18 is disengaged, the barbs 23 anchor the proximal end of the prosthesis 20 to the lumen. The wire stent 17 is well suited for highly angulated lumens, and may provide sufficient expansion of the prosthesis 20 at all points along the lumen to form a seal. Preferably, the self expanding portion of the prosthesis 20 uses stents 19 that provide just enough radial force to expand the prosthesis 20 to the vicinity of the lumen interior surface, while the wire stent 17 provides force for sealing the prosthesis 20 to the lumen interior surface.

Figure 2:
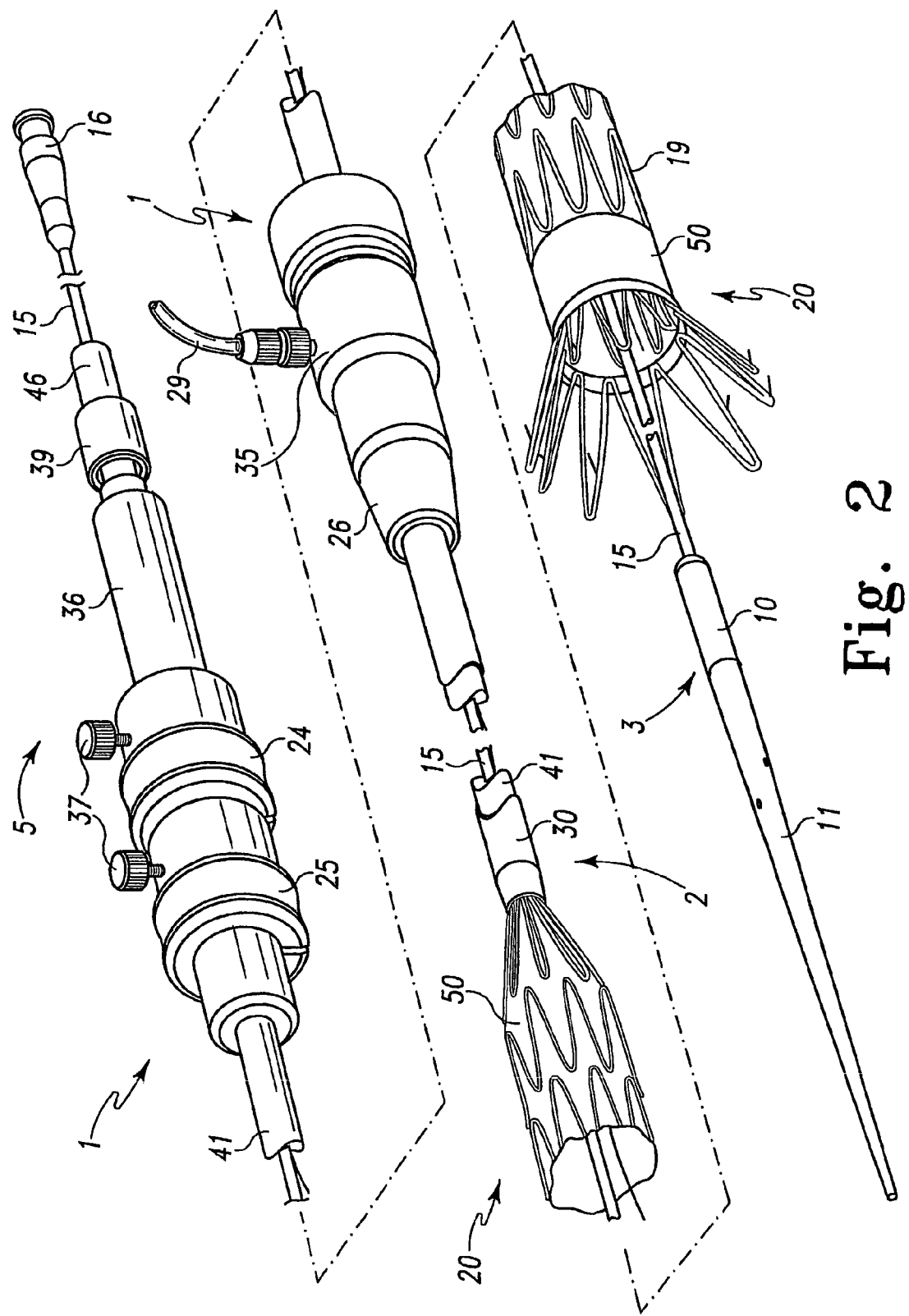
FIG. 2 shows a first introducer in perspective view with a prosthesis of the present invention partially deployed.

FIG. 2 shows an endovascular deployment system, also known as an introducer 5, for deploying the prosthesis 20 in a lumen of a patient during a medical procedure. The introducer 5 shown in FIG. 2 includes an external manipulation section 1, a distal positioning mechanism and attachment region 2 and a proximal positioning mechanism and attachment region 3. During the medical procedure to deploy the prosthesis 20, the distal and proximal attachment regions 2 and 3 will travel through the lumen to a desired deployment site. The external manipulation section 1, which is acted upon by a user to manipulate the introducer 5, remains outside of the patient throughout the procedure.

The external manipulation section 1 includes a body 36 that is mounted onto a thick walled plastic tube 41. A thin walled tube 15 passes through the body 36. A connector 16 on the end of the thin walled tube 15 is adapted to accept a syringe to facilitate the introduction of reagents into the tube 15. A proximal wire release mechanism 24 is mounted for slidable movement on the body 36. Similarly, a distal wire release mechanism 25 is mounted for slidable movement on the body 36. A pair of clamping screws 37 prevents inadvertent movement of the wire release mechanisms 24 and 25 relative to the body 36. A pin vise 39 is mounted onto the distal end of the body 36 that has a screw cap 46 that controls the movement of thin walled tube 15 with respect to the body 36. A clamping collar 26 surrounds the thick wall plastic tube 41. A sheath 30 surrounds the thick wall plastic tube 41 and is coupled to the clamping collar 26 that is fixed to a haemostatic sealing assembly 35. A side tube 29 on the sealing assembly 35 facilitates the introduction of medical reagents between the thick walled tube 41 and the sheath 30.

Figure 3:
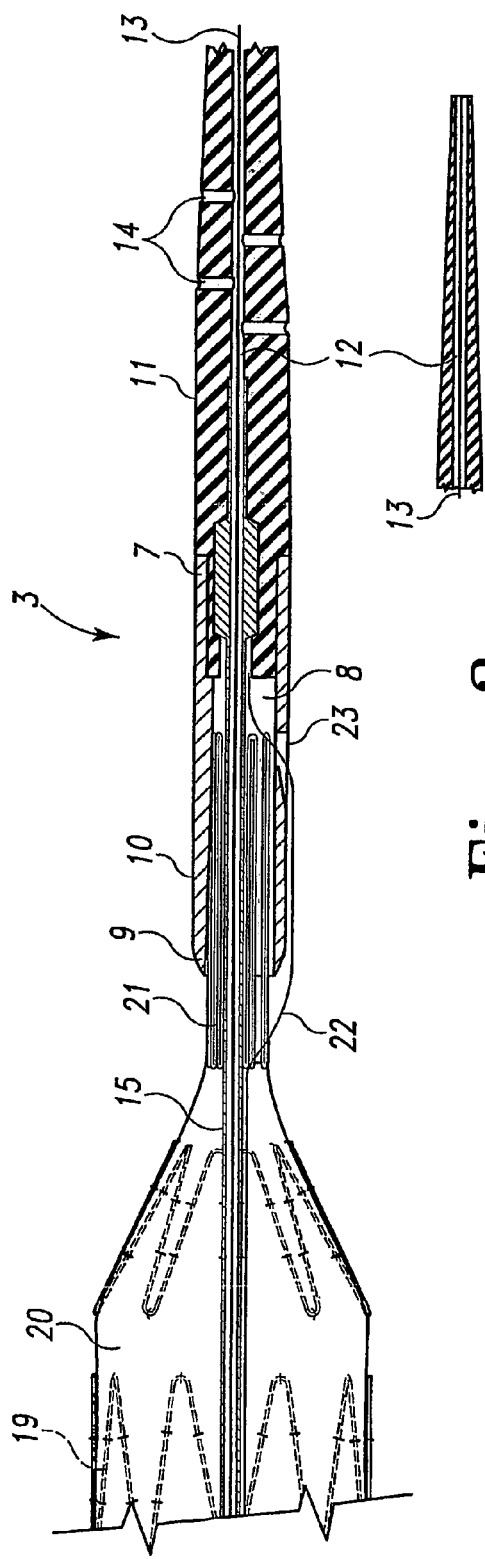
FIG. 3 shows a portion of the introducer around the proximal end of the prosthesis in detail.

The proximal positioning mechanism and attachment region 3 includes a cylindrical sleeve 10 and a long tapered flexible extension 11, which are shown in greater detail in FIG. 3. A distal end 9 of the cylindrical sleeve 10 includes a chamber 8 adapted to receive the proximal end of the prosthesis 20. A proximal end 7 of the cylindrical sleeve 10 is coupled to a long tapered flexible extension 11. The flexible extension 11 has an internal longitudinal aperture 12. The longitudinal aperture 12 facilitates advancement of the tapered flexible extension 11 along an insertion wire 13. The longitudinal aperture 12 also provides a channel for the introduction of medical reagents, which can flow out through lateral openings 14. For example, a contrast agent can be supplied through the longitudinal aperture 12 and lateral openings 14 to allow angiography to be performed during placement and deployment phases of a medical procedure. The thin walled metal tube 15 is fastened to the extension 11. The thin walled metal tube 15 is flexible so that the introducer 5 can be advanced along a relatively tortuous vessel, such as a femoral artery, and also to allow manipulation longitudinally and rotationally of the proximal attachment region 3. The thin walled metal tube 15 extends through the introducer 5 from the extension 11 to the manipulation section 1, terminating at the connector 16.

Figure 4:
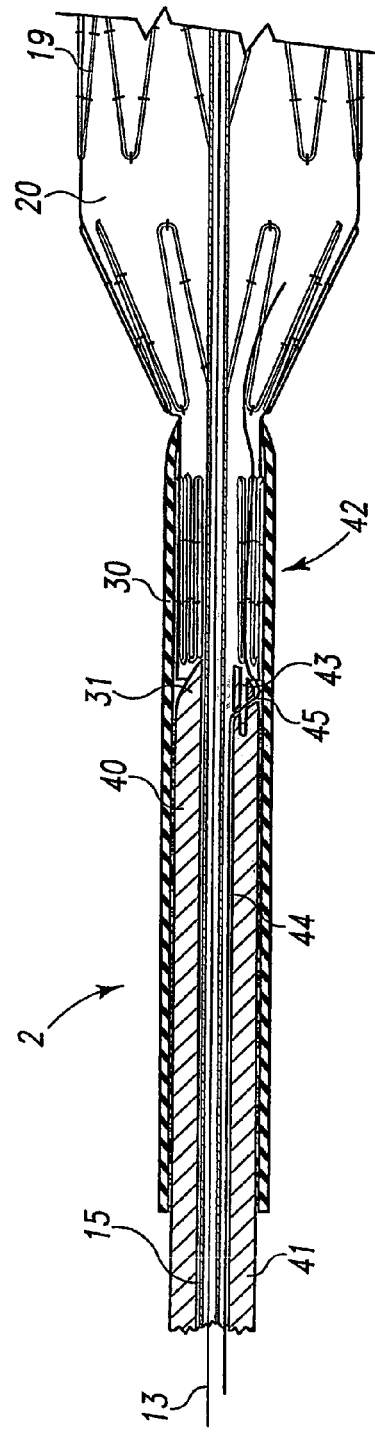
FIG. 4 shows a portion of the introducer around the distal end of the prosthesis in detail.
Figure 5:
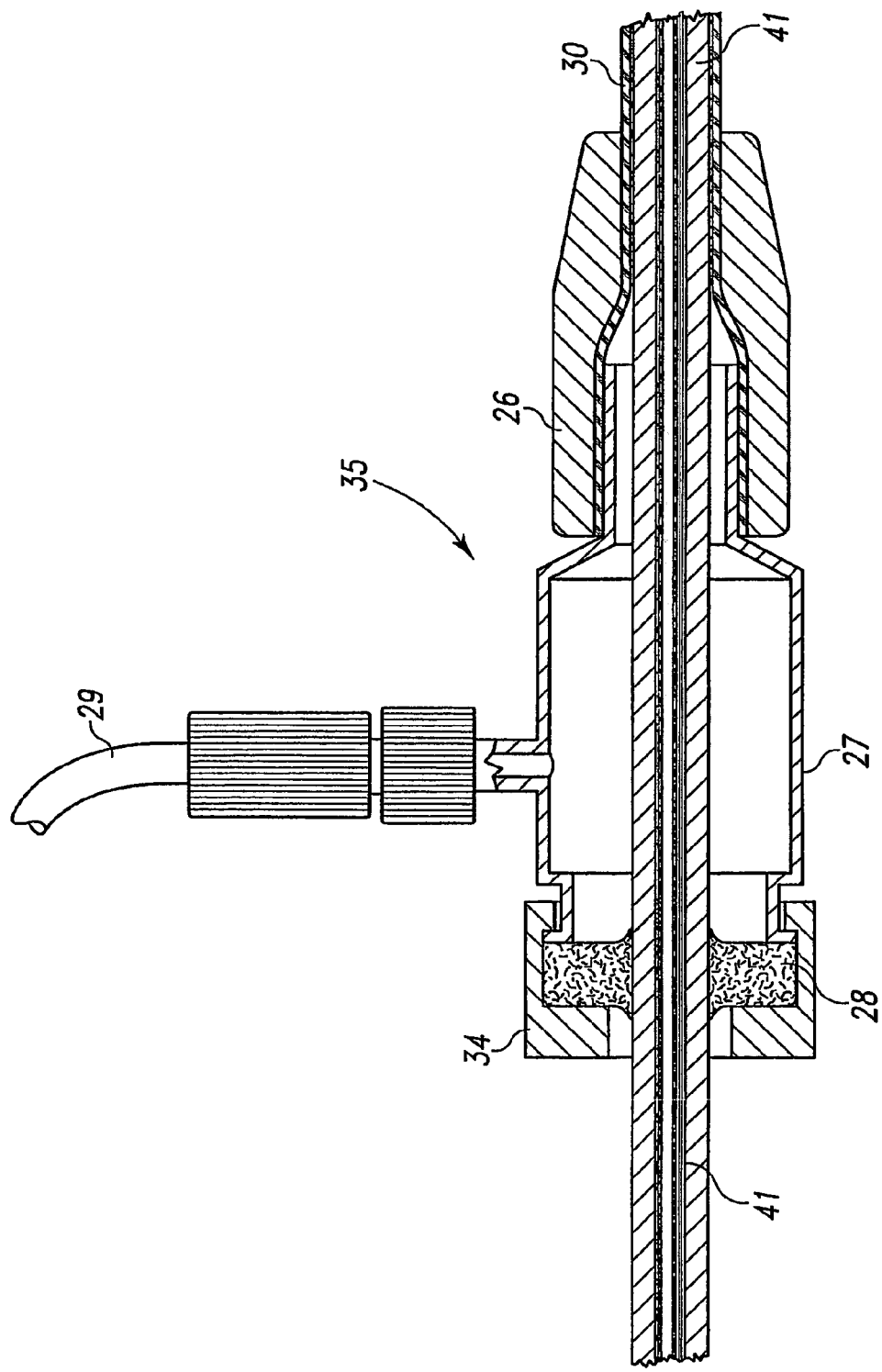
FIG. 5 shows a portion of the introducer around the haemostatic seal in detail.

The distal positioning mechanism and attachment region 2 is shown in detail in FIG. 4, to include the proximal end portion 31 of the thick walled plastic tube 41 that is coaxial with and radially outside the thin walled metal tube 15. A distal attachment retention section 40 is formed in the thick walled plastic tube 41 to retain the distal end 42 of the prosthesis 20. The thickness of the plastic tube 41 is several times that of the thin walled metal tube 15. The sheath 30 is coaxial with and radially outside the thick walled tube 41. The thick walled plastic tube 41 and the sheath 30 extend distally to the manipulation region 1, as shown in FIGS. 1 and 5. The sheath 30 extends distally to the gripping collar 26 and haemostatic sealing assembly 35 of the external manipulation section 1, as shown in detail in FIG. 5.

The sheath 30 is longitudinally movable with respect to the thick walled plastic tube 41 by manipulation of the clamping collar 26. The haemostatic sealing assembly 35 includes a chamber 27 and the side tube 29. The clamping collar 26 engages the proximal end of chamber 27 and clamps the sheath 30 to the chamber 27. A seal ring 28, typically made of silicone, is coupled to the distal end of the chamber 27 by a compression fitting 34 that ensures a haemostatic seal around the thick walled tube 41. The side tube 29 facilitates the introduction of medical reagents between the thick walled tube 41 and the sheath 30.

Figure 6:
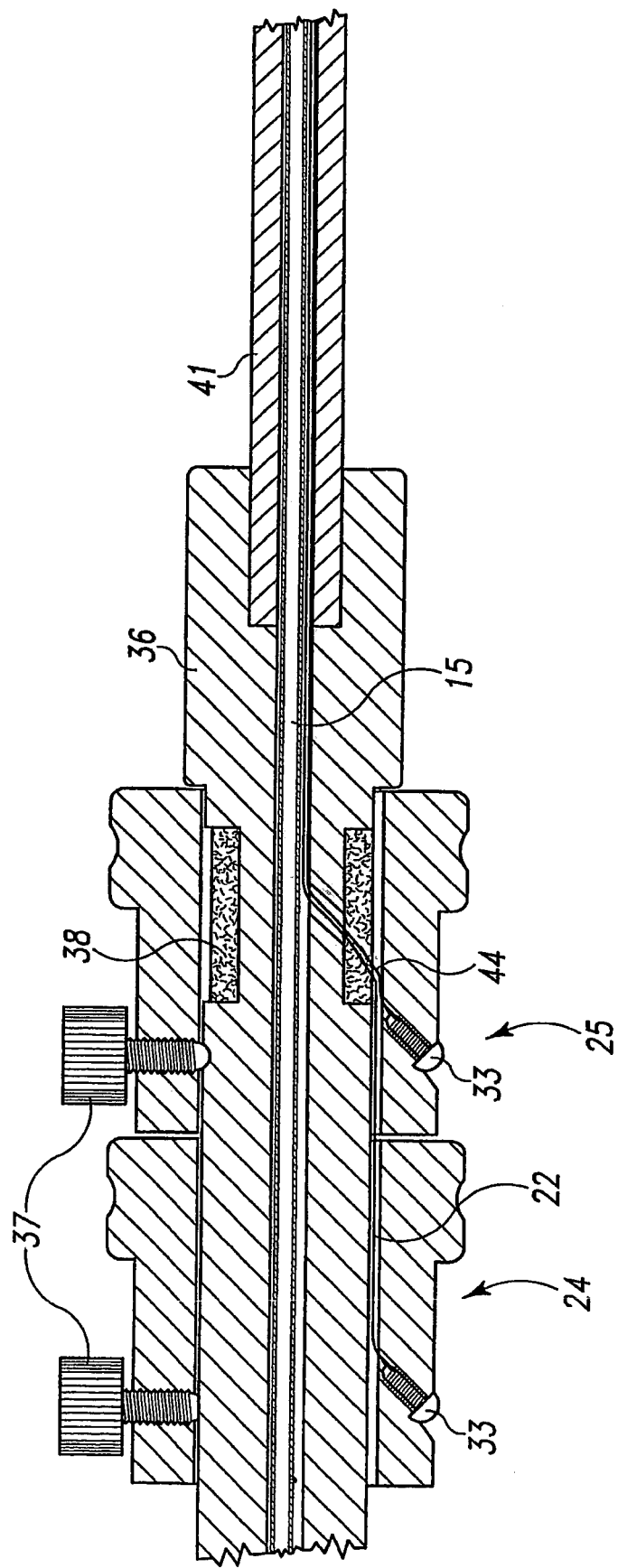
FIG. 6 shows a portion of the introducer around the trigger wire release mechanisms in detail.

The release wire actuation section 32 of the external manipulation section 1 is shown in FIG. 6 to have a body 36 that is fixed to the thick walled plastic tube 41. The thin walled tube 15 passes through the body 36. The proximal wire release mechanism 24 and distal wire release mechanism 25 are mounted for slidable movement on the body 36. A pair of clamping screws 37 prevents inadvertent movement of the wire release mechanisms 24 and 25 that could possibly lead to early release of the prosthesis 20. The positioning of the proximal and distal wire release mechanisms 24 and 25 is such that the proximal wire release mechanism 24 must be moved before the distal wire release mechanism 25 can be moved. The proximal and distal wire release mechanisms 24 and 25 are connected to release wires 22 and 44, respectively.

The release wire 22 extends forward from the proximal wire release mechanism 24 through a space between the thin walled tube 15 and the thick walled plastic tube 41, and through the interior of the prosthesis 20 to the junction between the cylindrical sleeve 10 and the tapered flexible extension 11 as shown in FIG. 3. The proximal end of the release wire 22 can be frictionally held between the tapered flexible extension 11 and the proximal end of the thin walled tube 15 to inhibit any proximal movement of the cylindrical sleeve 10 and the tapered flexible extension 11 with respect to the prosthesis 20. The release wire 22 and the proximal wire release mechanism 24 form a control to selectively permit disengagement of the cylindrical sleeve 10 from the prosthesis 20 and self expanding zigzag stent 18 when positioned at a desired site in a lumen.

The release wire 44 extends forward from the proximal wire release mechanism 25 through the space between the thin walled tube 15 and the thick walled plastic tube 41. The release wire 44 extends through a loop 43 in the distal end 42 of the prosthesis 20 as shown in FIG. 4. The distal release wire 44 also extends through an aperture 45 in the distal attachment section 40 into the annular region between the thin walled tube 15 and the thick walled tube 41. The distal release wire 44 and the distal wire release mechanism 25 form a control member to permit selective disengagement of the distal retention section 40 from the prosthesis 20 when positioned at a desired site in a lumen. The relative positions of the release mechanisms 24 and 25 on the body 36 ensures that the distal end 42 of the prosthesis 20 cannot be released until the self-expanding zigzag stent 18 has been released. A haemostatic seal 38 is provided so that release wires 22 and 44 can extend out through the body 36 to the release mechanisms 24 and 25 without unnecessary blood loss during the medical procedure. The release wires 22 and 44 can be coupled to wire release mechanisms 24 and 25, respectively, by fasteners 33.

Figure 7:
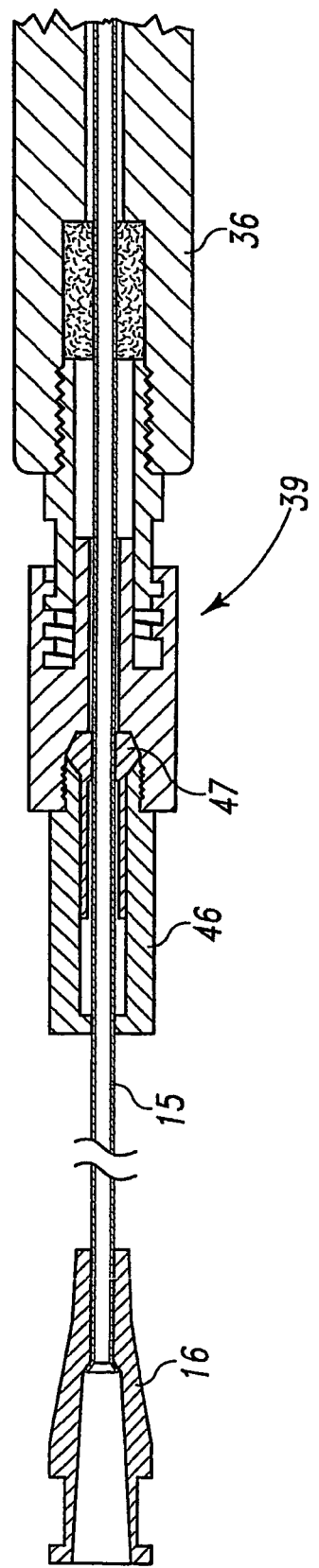
FIG. 7 shows a portion of the introducer around the pin vise clamp and the medical reagent introduction tube in detail.

FIG. 7 shows the distal portion of the external manipulation section 1 that includes the pin vise 39, which is mounted onto the distal end of the body 36. The pin vise 39 has a screw cap 46 that includes vise jaws 47. When screwed in, the vise jaws 47 clamp against and engage the thin walled metal tube 15. When the vise jaws 47 are engaged, the thin walled tube 15 can only move with the body 36, and hence the thin walled tube 15 can only move with the thick walled tube 41. With the screw cap 46 tightened, the entire assembly must be moved as one, except for the external sleeve 30 and structure coupled thereto as shown in FIG. 5. FIG. 7 also shows the connector 16 that is adapted to accept a syringe to facilitate the introduction of reagents into the metal tube 15. The metal tube 15 is in fluid communication with the aperture 12 of the flexible extension 11. Therefore, reagents introduced into connector 16 can flow through the aperture 12 and emanate from the lateral openings 14.

Figure 8:
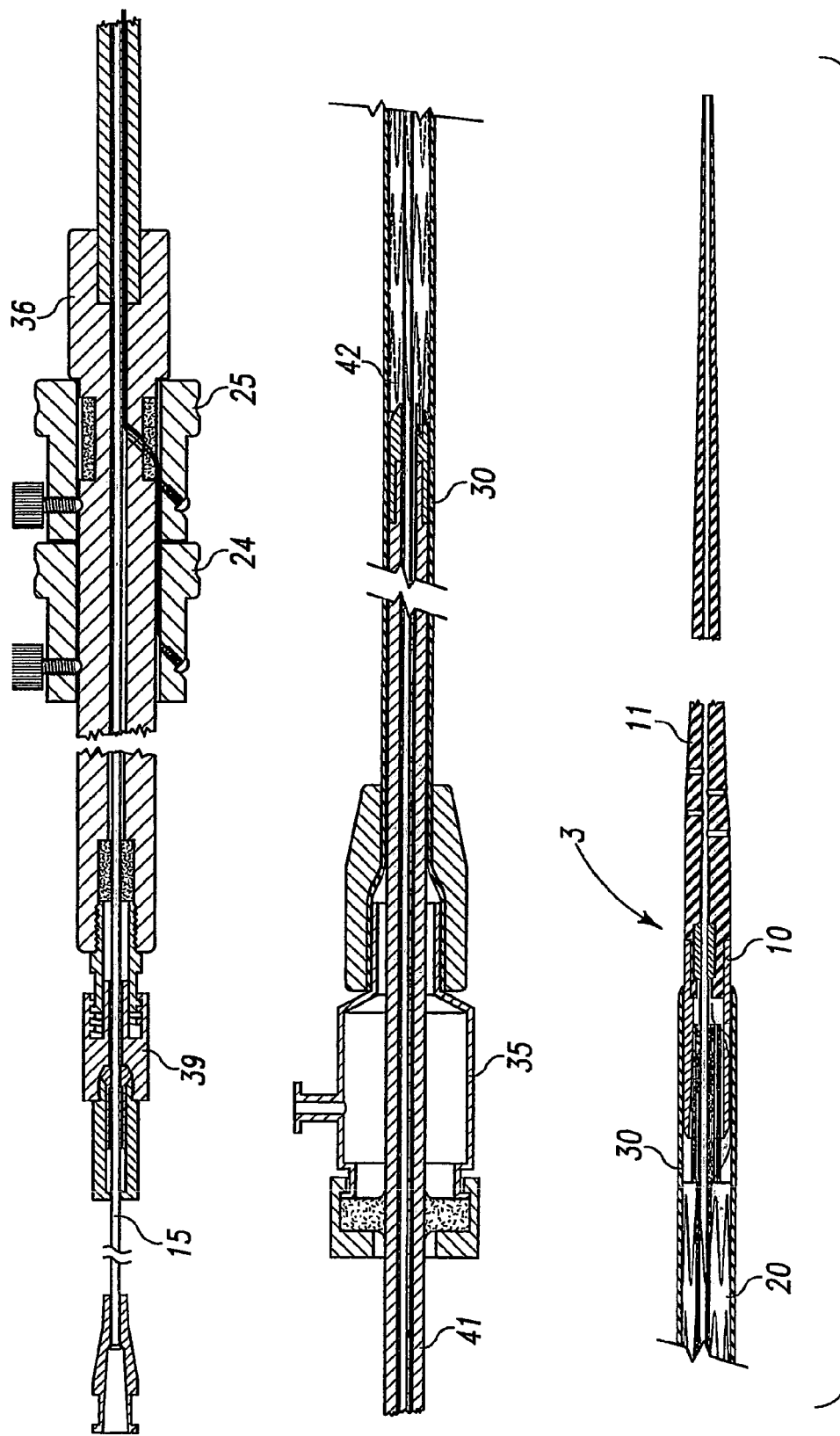
FIG. 8 shows a introducer of FIG. 1 fully loaded and ready for introduction into a patient.

During assembly of the combined introducer 5 and prosthesis 20, the sheath 30 is advanced over the cylindrical sleeve 10 of the proximal attachment region 3 while the prosthesis 20 is held in a compressed state by an external force. During the placement phase, the prosthesis 20 is retained in a compressed condition by the sheath 30, the sheath 30 extending proximally beyond the proximal end 31 of the thick walled plastic tube 41 to mate with the cylindrical sleeve 10 as shown in FIG. 8. The distal end 42 of the prosthesis 20 is retained by the distal attachment section 40 of the thick walled tube 41. Alternatively, the distal attachment section 40 may be a separate piece coupled to the thick walled plastic tube 41. In FIG. 8, the introducer 5 and prosthesis 20 assembly is shown fully assembled ready for introduction into a patient. The prosthesis 20 is retained at each of its ends by the proximal and distal retaining assemblies respectively, and compressed by the external sleeve 30. If an aortic aneurism is to be grafted, the introducer assembly 5 can be inserted through a femoral artery over a guide wire 13, and positioned by radiographic techniques (not discussed here). Any fenestration present in the prosthesis 20 may be aligned with a branch vessel, such as a renal artery, during this positioning.

The prosthesis 20 can be deployed in any method known in the art, preferably the method described in WO98/53761 in which the devise is inserted by the introducer 5 via a surgical cut-down into a femoral artery, and then advanced into the desired position over a stiff wire guide 13 using endoluminal interventional techniques. For example, FIGS. 8 through 13 show various stages of the deployment of the prosthesis 20 during an illustrative medical procedure. A guide wire 13 is introduced into the femoral artery and advanced until its tip is beyond the region into which the prosthesis 20 is to be deployed.

The prosthesis 20 is then released by first retracting the sheath 30. The retraction is accomplished by moving the gripping collar 26 and haemostatic sealing assembly 35 distally along the thick walled tube 41 to the position shown in FIG. 9. The external sheath 30 is withdrawn to just proximal of the distal attachment section 40. This action releases the central portion 28 of the prosthesis 20 so that the prosthesis central portion 28 can expand radially. The proximal self-expanding stent 18, however, is still retained within the chamber 8 of the cylindrical sleeve 10. Also, the distal end 42 of the prosthesis 20 is still retained within the external sheath 30. The retraction of the sheath 30 allows the central portion 28 of the prosthesis 20 located between the attachment section 40 of the thick walled tube 41 and the cylindrical sleeve 10 to expand outwardly to contact and conform to the lumen, including any arching portion of the lumen.

Figure 10:
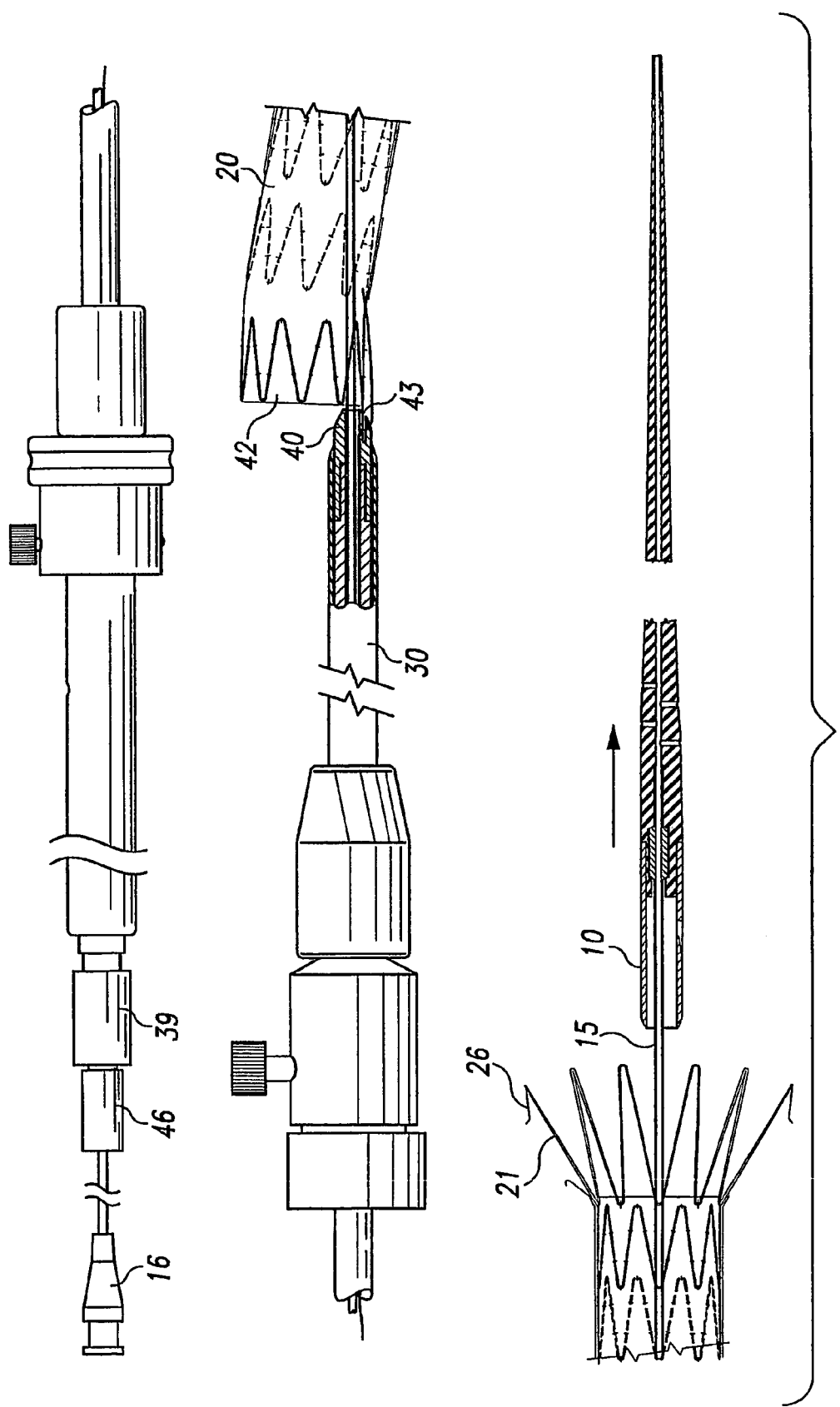
FIG. 10 shows the introducer of FIG. 8 with the release of the proximal end stage of deployment.

Next, the release wire 22 is pulled from its connection between the tapered flexible extension 11 and the proximal end of the thin walled tube 15. This is accomplished by releasing the clamping screw 37 holding the proximal wire release mechanism 24 to the body 36, and then sliding the proximal wire release mechanism 24 off the distal end of the external manipulation section 1. This frees the attachment region 3, including the cylindrical sleeve 10, for movement proximally away from the prosthesis 20. This movement is accomplished by releasing the screw cap 46 of the pin vise 39 so that the thin walled tubing 15 can been pushed in a proximal direction to move the cylindrical sleeve 10 in a proximal direction. When the cylindrical sleeve 10 no longer surrounds the self-expanding stent 18 at the proximal end of the prosthesis 20, the self-expanding stent 18 expands as shown in FIG. 10. When the self-expanding stent 18 expands, the hooks or barbs 23 on the self-expanding stent 18 grip into the walls of the lumen to hold the proximal end of the prosthesis 20 in place.

Figure 9:
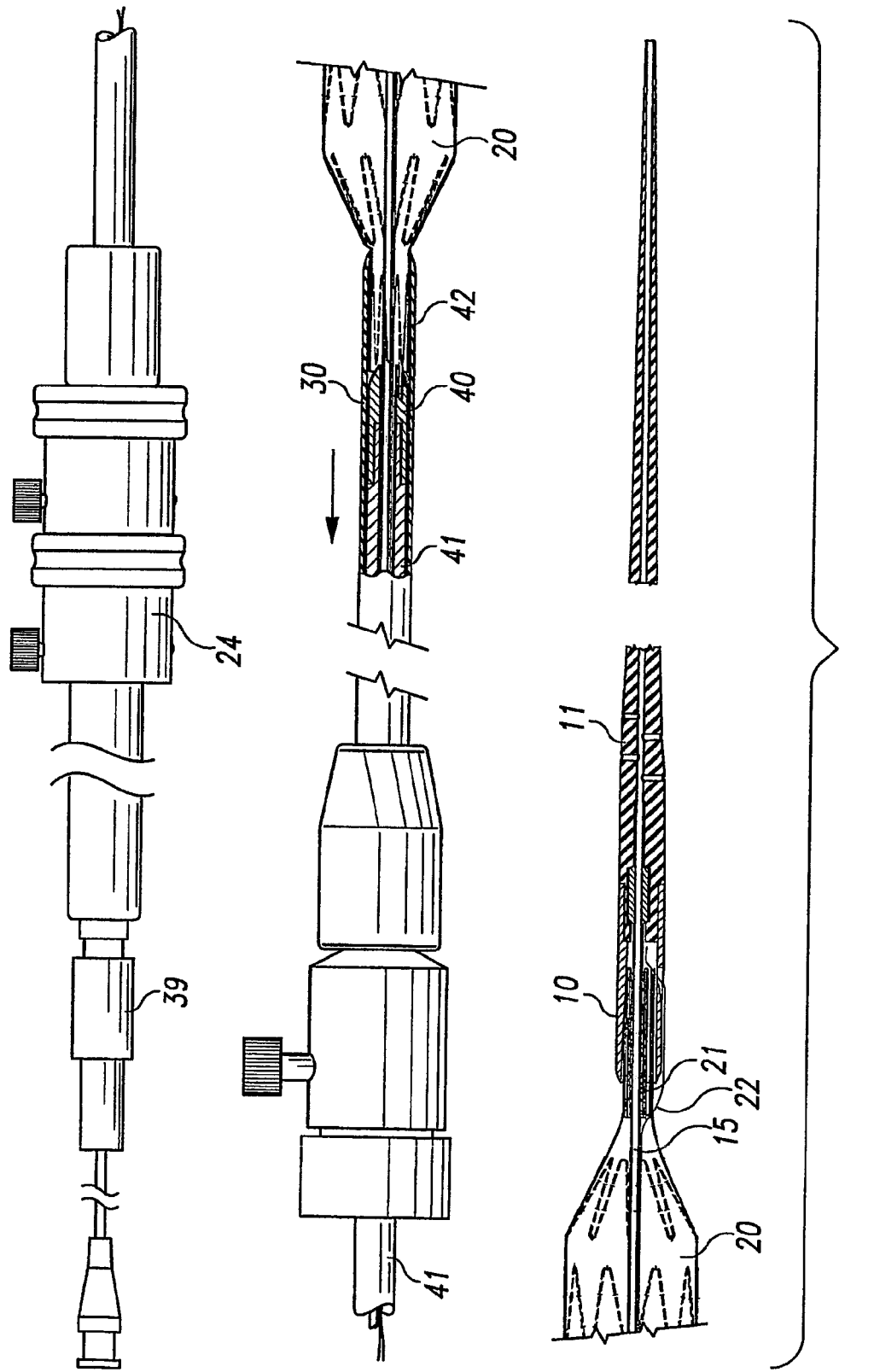
FIG. 9 shows a introducer of FIG. 8 in the next stage of deployment of the prosthesis.

At this point, the distal end 42 of the prosthesis 20 is still retained by the distal attachment section 40 as shown in FIG. 9, with the loop 43 retained therein as shown in FIG. 4. The external sheath 30 is then withdrawn to distal of the distal attachment section 40 to allow the distal end 42 of the prosthesis 20 to expand as shown in FIG. 10. Since the loop 43 is still connected, the distal end 42 of the prosthesis 20 may still be moved by manipulation of the external manipulation section 1. Consequently, the prosthesis 20 can still be rotated or lengthened or shortened or otherwise moved to for accurate positioning.

Figure 11:
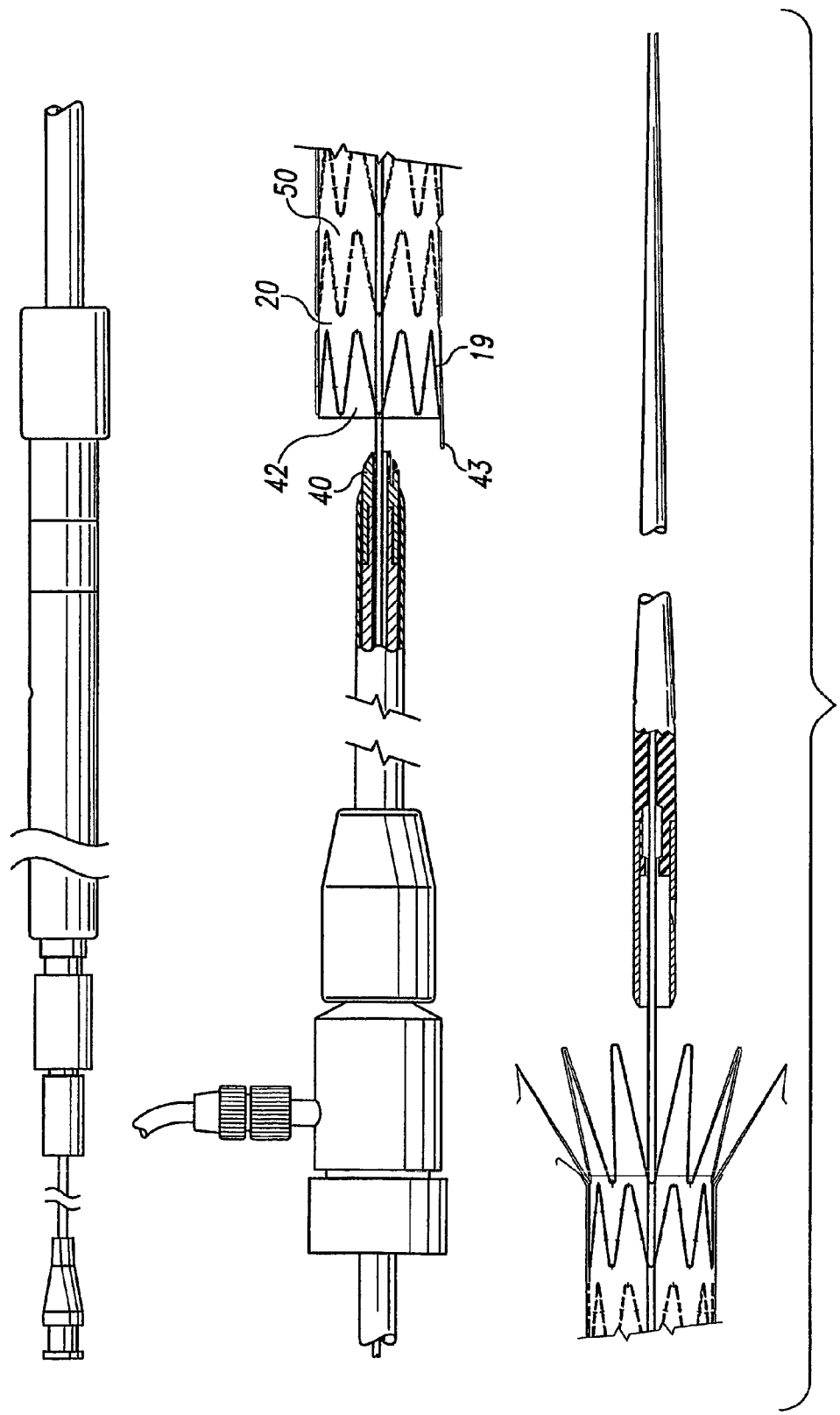
FIG. 11 shows the introducer of FIG. 8 with the release of the distal end stage of deployment.

Next, the distal release wire 44 is removed and the distal end 42 of the prosthesis 20 released as shown in FIG. 11. This is accomplished by releasing the clamping screw 37 holding the proximal wire release mechanism 24 to the body 36, and then sliding the distal wire release mechanism 25 over the pin vise 39 and the connector 16 and off the distal end of the external manipulation section 1. With the removal of the distal release wire 44, the loop 43 of the terminal distal self-expanding zigzag stent 19 is released, and the full extent prosthesis 20 is now free to conform to the wall of the lumen as shown in FIG. 11. At this point, the introducer 5 is ready to be removed.

Figure 12:
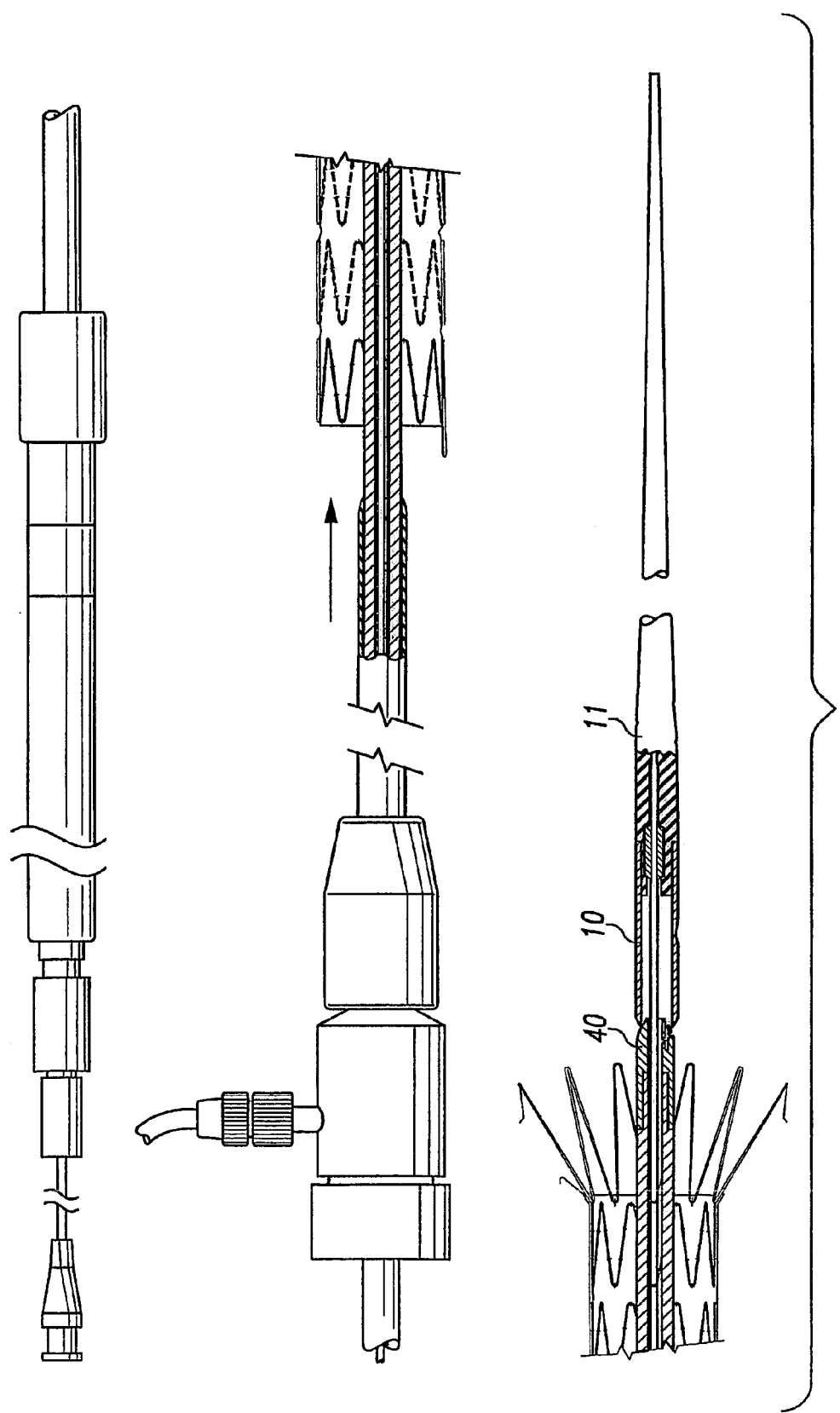
FIG. 12 shows the advancement of the distal attachment mechanism to the proximal attachment mechanism.
Figure 13:
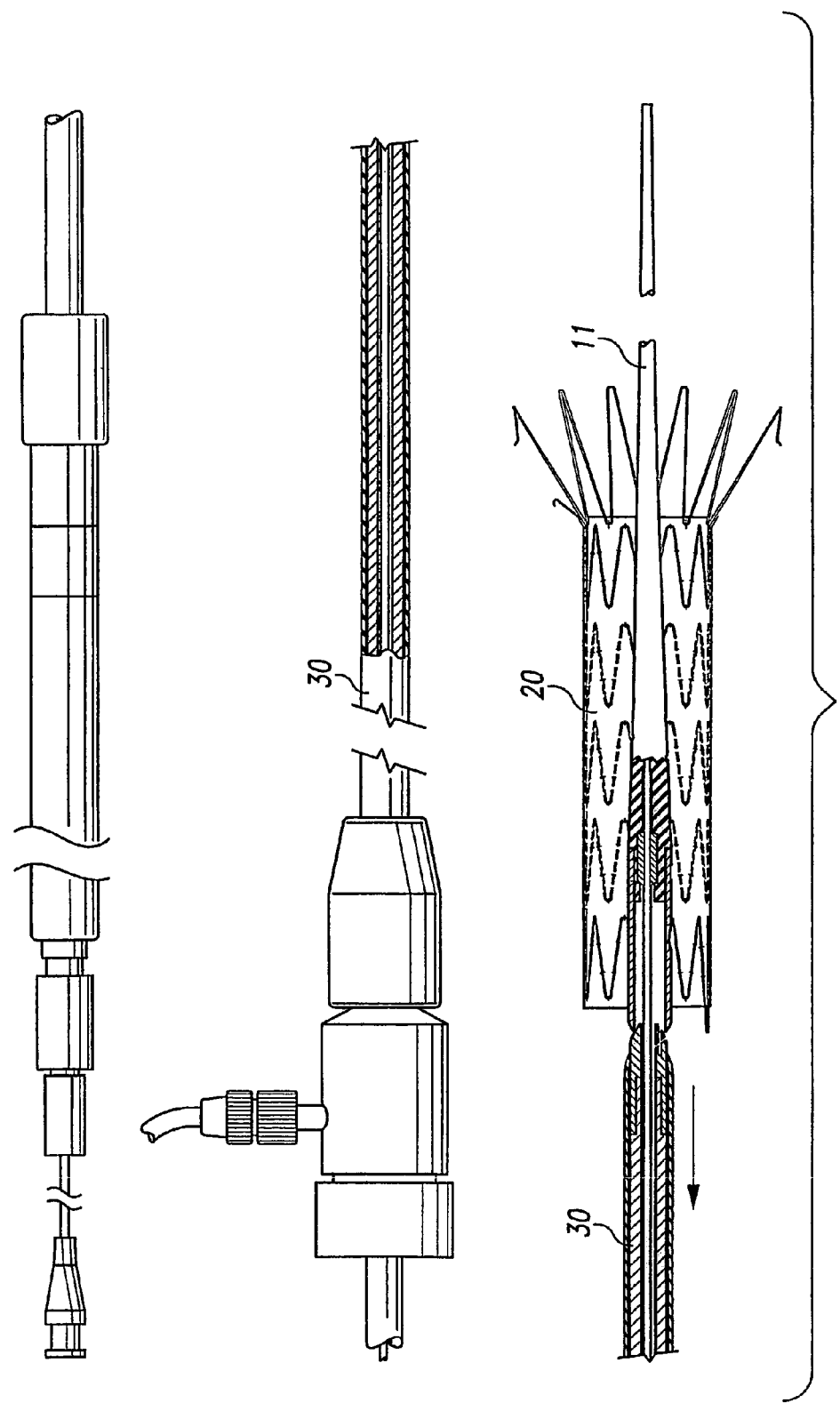
FIG. 13 shows the withdrawal of the introducer.

The first stage of removal is shown in FIG. 12. First, the distal attachment section 40 is advanced until being received in the rear of the proximal attachment device 10. Next, the sheath 30 can be advanced, if desired, to cover the region between the cylindrical sleeve 10 and the distal attachment section 40. Next, the cylindrical sleeve 10, the tapered flexible extension 11, and the distal attachment section 40 are removed together with the sheath 30 by withdrawing the introducer 5 distally from the lumen and the patient as shown in FIG. 13. Alternatively, these items could be removed separately, followed by removal of the external sleeve 30.

Figure 14:
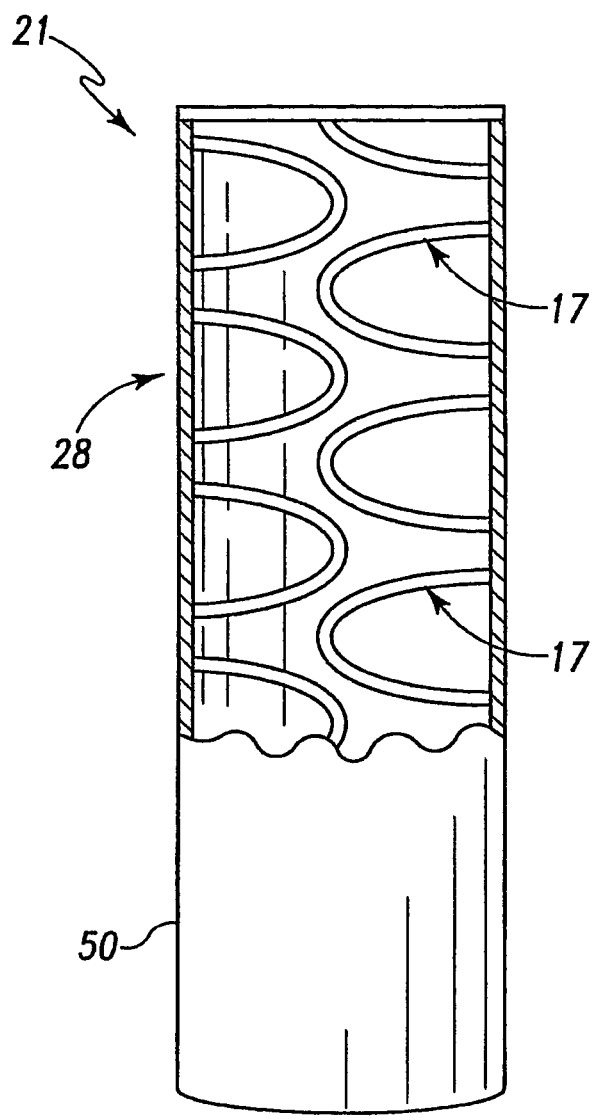
FIG. 14 is a side elevation view, partially cut away, of another prosthesis of the present invention.

An alternate embodiment of a prosthesis 21 is shown in FIG. 14 to include a tubular graft 50 and, in a central portion 28, a wire stent 17 of the Gianturco-Rueben type. The embodiment shown in FIG. 2 could allow for the prosthesis 21 to be delivered via smaller diameter delivery system than the embodiment shown in FIG. 1. The balloon expandable prosthesis 21 could be deployed as part of a main introducer system having a balloon attached thereto, or delivered separately.

Figure 15:
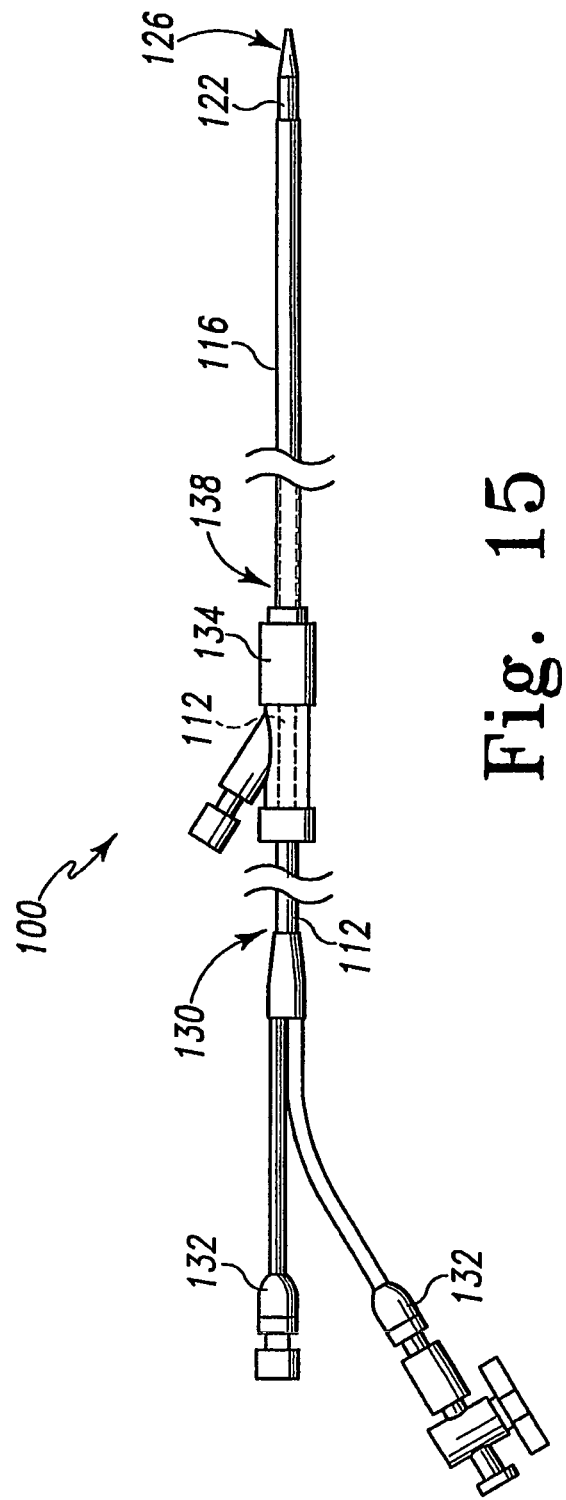
FIG. 15 is an endovascular introducer for deploying expanding a stent of the prosthesis of FIG. 14.

FIG. 15 shows an endovascular introducer 100 with an inflatable balloon 122 for expanding the wire stent 17 of the prosthesis 21. After the prosthesis 21 is implanted at the desired site in the lumen, as described above, the endovascular introducer 100 is positioned in the lumen so that the balloon 122 is inside the wire stent 17. The introducer 100 may comprise a catheter 112 and a sleeve 116 carried on the catheter 112. The inflatable balloon 122 is carried on the catheter 112 near the distal tip 126 of the catheter 112. One or more fluid couplings 132 are provided at the proximal end 130 of the catheter 112, through which a pressurized fluid is supplied to the balloon 122 through a lumen for inflation. The introducer 100 may be similar to the introducers disclosed in U.S. Pat. No. 6,447,540 entitled "Stent Deployment Device Including Splittable Sleeve Containing the Stent", which is herein incorporated by reference.

The sleeve 116 may be substantially the same length as the catheter 112 and include a proximal end 138 fixed to the catheter 112, for example, fixed near the proximal end 130 of the catheter 112 at the coupling 134. The sleeve 116 can be composed of any of a variety of materials, some more suited to particular applications than others. The sleeve 116 may be composed of an indistensable material. The sleeve 116 may also be composed of a medical grade material, which can be either physiologically inert or biodegradable. Although not depicted, another lumen extends longitudinally through the catheter between the distal end thereof and one of the proximal couplings 132. This lumen is typically utilized for passing the catheter over a wire guide that has already been positioned in a vessel.

Inflation of the balloon with the fluids need only proceed for the balloon to extend radially outwardly to expand the sleeve. Preferably, the wire stent 17 is expanded by expansion of the balloon 122 during its inflation by the fluid. Once the wire stent 17 has been expanded, the balloon 122 may be deflated, and the introducer 100 can be removed from the lumen.

Throughout this specification, unless the context requires otherwise, the words "comprise" and "include" and variations such as "comprising" and "including" will be understood to imply the inclusion of an item or group of items, but not the exclusion of any other item or group items.

While various embodiments of the invention have been described, it will be apparent to those of ordinary skill in the art that many more embodiments and implementations are possible within the scope of the invention. Furthermore, although various indications have been given as to the scope of this invention, the invention is not limited to any one of these but may reside in two or more of these combined together. Accordingly, the invention is not to be restricted except in light of the attached claims and their equivalents.

The invention claimed is:

1. An intraluminal prosthesis for placement in a body lumen having an interior surface, the prosthesis comprising:
    a tubular graft comprising a hollow flexible body and a graft lumen, the hollow flexible body having a proximal end and a distal end, and an exterior surface and an interior surface along the graft lumen;
    at least one self-expanding stent coupled along the exterior surface of the hollow flexible body; and
    a balloon expandable tubular stent, discrete from the at least one self-expanding stent, coupled to the interior surface along the graft lumen at the proximal end of the hollow flexible body and axially adjacent the at least one self expanding stent, the balloon expandable tubular stent having a first diameter and a second expanded diameter;
    wherein the balloon expandable tubular stent is expandable to the second diameter by application of an outwardly extending force from an interior of the balloon expandable tubular stent, and the second diameter is at least equal to an interior diameter of the graft lumen of the tubular graft;
    where the at least one self expanding stent has a radial force just enough to expand and maintain the hollow flexible body in an expanded configuration so that patency of the graft lumen is maintained, and the balloon expandable tubular stent has a radial force sufficient to seal the proximal end of the tubular graft to the interior surface of said body lumen, and
    where the radial force of the self-expanding stent is independent of the radial force of the balloon expandable tubular stent and less than the radial force of the balloon expandable stent.

2. The intraluminal prosthesis of claim 1 wherein the at least one self-expanding stent comprises a plurality of self-expanding stents that are coupled along a length of a portion of the hollow flexible body.

3. The intraluminal prosthesis of claim 1 wherein the balloon expandable tubular stent comprises an elongated member with a passage extending longitudinally there through.

4. The intraluminal prosthesis of claim 1 wherein the balloon expandable tubular stent comprises stainless steel.

5. The intraluminal prosthesis of claim 1 wherein the tubular graft comprises a derived collagen material.

6. The intraluminal prosthesis of claim 5 wherein the derived collagen material is an extracellular matrix.

7. The intraluminal prosthesis of claim 6 wherein the extracellular matrix is small intestinal submucosa.

8. The intraluminal prosthesis of claim 6 wherein the extracellular matrix is stomach submucosa.

9. The intraluminal prosthesis of claim 6 wherein the extracellular matrix is pericardium.

10. The intraluminal prosthesis of claim 6 wherein the extracellular matrix is liver basement membrane.

11. The intraluminal prosthesis of claim 6 wherein the extracellular matrix is urinary bladder submucosa.

12. The intraluminal prosthesis of claim 1 wherein the tubular graft comprises a synthetic material.

13. The intraluminal prosthesis of claim 12 wherein synthetic material is a polyester.

14. The intraluminal prosthesis of claim 12 wherein synthetic material is polytetrafluoroethylene.

15. The intraluminal prosthesis of claim 12 wherein synthetic material is expanded polytetrafluoroethylene.

16. The intraluminal prosthesis of claim 1, wherein the radial force of the balloon expandable tubular stent is greater than the radial force of the at least one self-expanding stent.

17. An intraluminal prosthesis for placement in a body lumen having an interior surface, the prosthesis comprising:
- a tubular graft comprising a hollow flexible body and a graft lumen and having a proximal end and a distal end, the hollow flexible body having an exterior surface and an interior surface along the graft lumen;
- a first self-expanding stent coupled to and extending past the proximal end of the tubular graft;
- a plurality of second self-expanding stents coupled along a length of the exterior surface of the hollow flexible body, the second self-expanding stents having a radial force just enough to expand and maintain the hollow flexible body in an expanded configuration so that patency of the graft lumen is maintained; and
- a balloon expandable tubular stent, discrete from the first and second self-expanding stents coupled along a length of the interior surface of the hollow flexible body at the proximal end, the balloon expandable tubular stent positioned axially adjacent the first self expanding stent and the second self-expanding stents, the balloon expandable tubular stent having a first diameter and a second expanded diameter,
- wherein the balloon expandable tubular stent is expandable to the second diameter by application of an outwardly extending force from an interior of the balloon expandable tubular stent, and the second diameter is at least equal to an interior diameter of the graft lumen of the tubular graft; and where the balloon expandable tubular stent has a radial force sufficient to seal the proximal end of the tubular graft to the interior surface of said lumen, and
- where the radial force of the self-expanding stents is independent of the radial force of the balloon expandable tubular stent and less than the radial force of the balloon expandable stent.

18. The intraluminal prosthesis of claim 17, wherein the first self-expanding stent comprises barbs to anchor said prosthesis to a selected location within said lumen.

19. The intraluminal prosthesis of claim 17, wherein the radial force of the balloon expandable tubular stent is greater than the radial force of the second self-expanding stents.

20. An intraluminal prosthesis for placement in a body lumen having an interior surface, the prosthesis comprising:
- a tubular graft comprising a hollow flexible body and a graft lumen and having a proximal end and a distal end, the body having an exterior surface and an interior surface along the graft lumen;
- a plurality of self-expanding stents coupled along a length of the exterior surface of the body, the self-expanding stents having a radial force just enough to expand and maintain the hollow flexible body in an expanded configuration so that patency of the graft lumen is maintained; and
- one or more balloon expandable tubular stents, discrete from the self-expanding stents, coupled along a length of a portion of the interior surface of the body along the graft lumen, the balloon expandable tubular stent having a first diameter and a second expanded diameter,
- wherein the balloon expandable tubular stent is expandable to the second diameter by application of an outwardly extending force from an interior of the balloon expandable tubular stent, and the second diameter is at least equal to an interior diameter of the graft lumen of the tubular graft; and where the balloon expandable tubular stent has a radial force sufficient to seal the tubular graft to the interior surface of said lumen, the radial force of the balloon expandable tubular stent being greater than the radial force of the self-expanding stents, and
- where the radial force of the self-expanding stent is independent of the radial force of the balloon expandable tubular stent and less than the radial force of the balloon expandable stent.

* * * * *